US012608976B2

(12) United States Patent
Li et al.

(10) Patent No.: US 12,608,976 B2
(45) Date of Patent: Apr. 21, 2026

(54) METHOD AND SYSTEM FOR ASSISTING IN DETERMINING IDENTITY OF SCANNED PERSON IN CT SCANNING, AND CT SCANNER

(71) Applicant: Siemens Shanghai Medical Equipment Ltd., Shanghai (CN)

(72) Inventors: Ze Ben Li, Shanghai (CN); Li Na Li, Shanghai (CN); Jia Feng, Shanghai (CN); Jie Qing Liu, Shanghai (CN)

(73) Assignee: Siemens Shanghai Medical Equipment Ltd., Shanghai (CN)

( * ) Notice: Subject to any disclaimer, the term of this patent is extended or adjusted under 35 U.S.C. 154(b) by 299 days.

(21) Appl. No.: 18/577,733

(22) PCT Filed: Jul. 28, 2022

(86) PCT No.: PCT/CN2022/108743
§ 371 (c)(1),
(2) Date: Jan. 9, 2024

(87) PCT Pub. No.: WO2023/011323
PCT Pub. Date: Feb. 9, 2023

(65) Prior Publication Data
US 2024/0321006 A1 Sep. 26, 2024

(30) Foreign Application Priority Data
Aug. 4, 2021 (CN) .......................... 202110892009.8

(51) Int. Cl.
| | |
|---|---|
| *G06V 40/16* | (2022.01) |
| *A61B 6/03* | (2006.01) |
| *G06V 10/82* | (2022.01) |
| *G10L 17/22* | (2013.01) |

(52) U.S. Cl.
CPC ........... *G06V 40/172* (2022.01); *A61B 6/032* (2013.01); *G06V 10/82* (2022.01); *G10L 17/22* (2013.01)

(58) Field of Classification Search
None
See application file for complete search history.

(56) References Cited

U.S. PATENT DOCUMENTS

| | | |
|---|---|---|
| 2019/0366030 A1 | 12/2019 | Giap et al. |
| 2020/0008676 A1 | 1/2020 | Dong |
| 2022/0301717 A1* | 9/2022 | Xia ...................... G06V 40/174 |

FOREIGN PATENT DOCUMENTS

| | | |
|---|---|---|
| CN | 108664909 A | 10/2018 |
| CN | 109015690 A | 12/2018 |
| CN | 109379499 A | 2/2019 |
| CN | 111035404 A | 4/2020 |
| CN | 112245177 A | 1/2021 |
| DE | 102017220500 A1 | 5/2019 |
| WO | 2018160615 A1 | 9/2018 |

OTHER PUBLICATIONS

Aug. 11, 2022 (PCT) International Search Report and Written Opinion—App. PCT/CN2022/108743.

* cited by examiner

*Primary Examiner* — Lennin R RodriguezGonzalez
(74) *Attorney, Agent, or Firm* — Banner & Witcoff, Ltd.

(57) ABSTRACT

Techniques are provided for determining an identity of a scanned person in computed tomography (CT) scanning is provided. The techniques include the use of a system for assisting in determining an identity of a scanned person in CT scanning and a CT scanner.

13 Claims, 3 Drawing Sheets

METHOD AND SYSTEM FOR ASSISTING IN DETERMINING IDENTITY OF SCANNED PERSON IN CT SCANNING, AND CT SCANNER

CROSS-REFERENCE TO RELATED APPLICATIONS

The present application is a U.S. National Stage entry of PCT Application no. PCT/CN2022/108743, filed Jul. 28, 2022, which claims priority to and the benefit of China patent application no. CN 202110892009.8, filed on Aug. 4, 2021, the contents of each of which are incorporated herein by reference in their entireties.

TECHNICAL FIELD

The present disclosure provides a method for determining an identity of a scanned person, and, in particular, to a method for assisting in determining an identity of a scanned person in a computed tomography (CT) scan. The present disclosure further provides a system utilizing the above method for assisting in determining an identity of a scanned person in CT scanning, and a CT scanner.

BACKGROUND

In CT scanning, a doctor, as a CT device operator, sets a corresponding scanning program according to a patient as a scanned person. Therefore, the doctor needs to determine an identity of the patient before CT scanning. Currently, with a large number of received patients, the doctor under long-term high load work cannot accurately determine the identity of the scanned person due to the lack of concentration, resulting in the scanning program not corresponding to the patient.

SUMMARY

The objective of the present disclosure is to provide a method for assisting in determining an identity of a scanned person in CT scanning, which can assist an operator in determining an identity of a scanned person.

Another objective of the present disclosure is to provide a system for assisting in determining an identity of a scanned person in CT scanning, which can assist an operator in determining an identity of a scanned person.

Another objective of the present disclosure is to provide a CT scanner, which can assist an operator in determining an identity of a scanned person.

The present disclosure provides a method for assisting in determining an identity of a scanned person in CT scanning, including:

obtaining identity information of a scanned person;

collecting facial image information of the scanned person after the scanned person is positioned, and determining whether the scanned person is a match based on the identity information of the scanned person by using a facial recognition algorithm;

performing a voice dialogue with the scanned person based on the identity information of the scanned person by using natural language processing technology after the scanned person is positioned, and determining whether the scanned person is a match; and if either of determining results of the above determining is mismatching, sending a reminder of determining the identity of the scanned person to an operator and, if both determining results of the above determining are matching, starting a scan.

In the method for assisting in determining an identity of a scanned person in CT scanning, a facial image of the scanned person can be analyzed by using a facial recognition algorithm before a scanning program is started, and voice question and answer is performed with the scanned person by using natural language processing technology. It is determined, based on two independent manners, whether the identity of the scanned person is a match. If either of the determining results is mismatching, a reminder of determining the identity of the scanned person is sent to an operator, which ensures the accuracy of the determining results. The method for assisting in determining an identity of a scanned person in CT scanning can reduce the work intensity of the operator, increase work efficiency, prevent the occurrence of a false scan, and avoid diagnosis delay.

In another schematic implementation of the method for assisting in determining an identity of a scanned person in CT scanning, the collecting facial image information of the scanned person after the scanned person is positioned, and determining whether the scanned person is a match based on the identity information of the scanned person by using a facial recognition algorithm specifically includes:

photographing the scanned person through a camera to collect the facial image information;

building a convolutional neural network model based on a vision hardware platform and inputting the identity information of the scanned person and the facial image information;

extracting, by the vision hardware platform, facial feature information corresponding to the identity information of the scanned person by using the convolutional neural network model; and comparing the facial feature information with the identity information of the scanned person, and determining whether the scanned person is a match according to a comparison result.

In another schematic implementation of the method for assisting in determining an identity of a scanned person in CT scanning, the convolutional neural network model includes three processing units and two fully connected layers that are connected in series, each of the processing units includes a convolutional layer, an activation layer and a pooling layer, and the last one of the fully connected layers can output the facial feature information.

In another schematic implementation of the method for assisting in determining an identity of a scanned person in CT scanning, the performing a voice dialogue with the scanned person based on the identity information of the scanned person by using natural language processing technology after the scanned person is positioned, and determining whether the scanned person is a match specifically includes:

building a voice dialogue module based on a voice hardware platform and inputting the identity information of the scanned person;

analyzing, by the voice dialogue module, the identity information of the scanned person and generating corresponding question information;

playing, by the voice dialogue module, the question information to the scanned person through a speaker;

collecting, by the voice dialogue module, an answer voice of the scanned person through a microphone and converting the answer voice into answer information;

extracting, by the voice dialogue module, voice feature information corresponding to the identity information of the scanned person in the answer information according to preset logic; and comparing, by the voice dialogue module, the voice feature information with the identity information of the scanned person, and determining whether the scanned person is a match according to a comparison result.

In another schematic implementation of the method for assisting in determining an identity of a scanned person in CT scanning, the voice dialogue module includes a voice synthesis unit, a voice recognition unit, and a natural language processing unit. The voice synthesis unit is configured to convert the question information from a text information format into an audio information format. The voice recognition unit is configured to receive the answer voice in an audio information format, and convert the answer voice into the answer information a text information format. The natural language processing unit is configured to analyze the identity information of the scanned person and transmit the question information to the voice synthesis unit, and the natural language processing unit is further configured to receive the answer information from the voice recognition unit, extract the voice feature information and compare the voice feature information with the identity information of the scanned person after analysis, and determine whether the scanned person is a match according to a comparison result.

In another schematic implementation of the method for assisting in determining an identity of a scanned person in CT scanning, the identity information of the scanned person includes a name, gender, and age.

The present disclosure further provides a system for assisting in determining an identity of a scanned person in CT scanning, including a camera, a vision hardware platform, a speaker, a microphone, a voice hardware platform, and a reminder device. The camera is configured to collect facial image information of a scanned person after the scanned person is positioned. The vision hardware platform is built with a convolutional neural network model, where the vision hardware platform is configured to receive the identity information of the scanned person and the facial image information, and extract facial feature information corresponding to the identity information of the scanned person in the facial image information through the convolutional neural network model; and the vision hardware platform is configured to compare the facial feature information with the identity information of the scanned person, and generate an image mismatch signal in a case of mismatching. The speaker is configured to receive a sound signal and play a voice. The microphone is configured to receive a voice and convert the voice into a sound signal. The voice hardware platform is built with a voice dialogue module, where the voice dialogue module is configured to receive the identity information of the scanned person, and convert question information corresponding to the identity information of the scanned person into a sound signal and transmit the sound signal to the speaker; the voice hardware platform is further configured to receive, through the microphone, a sound signal answered by the scanned person and extract voice feature information corresponding to the identity information of the scanned person; and the voice hardware platform is configured to compare the voice feature information with the identity information of the scanned person, and generate a voice mismatch signal in a case of mismatching. The reminder device is configured to remind an operator when the image mismatch signal and the voice mismatch signal are received.

In another schematic implementation of the system for assisting in determining an identity of a scanned person in CT scanning, the convolutional neural network model includes three processing units and two fully connected layers that are connected in series. Each of the processing units includes a convolutional layer, an activation layer and a pooling layer, and the last one of the fully connected layers can output the facial feature information.

In another schematic implementation of the system for assisting in determining an identity of a scanned person in CT scanning, the voice dialogue module includes a voice synthesis unit, a voice recognition unit, and a natural language processing unit. The voice synthesis unit is configured to convert the question information from a text information format into an audio information format. The voice recognition unit is configured to receive the answer voice in an audio information format, and convert the answer voice into the answer information a text information format. The natural language processing unit is configured to analyze the identity information of the scanned person and transmit the question information to the voice synthesis unit, and the natural language processing unit is further configured to receive the answer information from the voice recognition unit, extract the voice feature information and compare the voice feature information with the identity information of the scanned person after analysis, and determine whether the scanned person is a match according to a comparison result. The system for assisting in determining an identity of a scanned person in CT scanning can reduce the work intensity of the operator, increase work efficiency, prevent the occurrence of a false scan, and avoid diagnosis delay.

In another schematic implementation of the system for assisting in determining an identity of a scanned person in CT scanning, the vision hardware platform and the voice hardware platform each may be a computer, a cloud server or a device with a system on a chip (SOC).

In another schematic implementation of the system for assisting in determining an identity of a scanned person in CT scanning, the vision hardware platform and the voice hardware platform are a processor unit of a CT scanner.

In another schematic implementation of the system for assisting in determining an identity of a scanned person in CT scanning, the reminder device includes a processor unit and an operation display screen of a CT scanner.

The present disclosure further provides a CT scanner, including the foregoing system for assisting in determining an identity of a scanned person in CT scanning. The CT scanner can reduce the work intensity of the operator, increase work efficiency, prevent the occurrence of a false scan, and avoid diagnosis delay.

BRIEF DESCRIPTION OF THE DRAWINGS

The following accompany drawings are only used for schematically describing and explaining the present disclosure, and do not constitute an inappropriate limitation on the present disclosure.

DESCRIPTION OF REFERENCE NUMBERS

Figure 1:
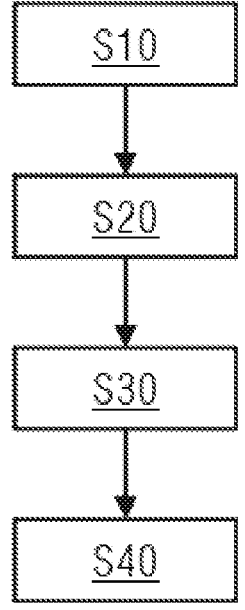
FIG. 1 illustrates a flowchart of a schematic implementation of a method for assisting in determining an identity of a scanned person in CT scanning, in accordance with one or more embodiments of the present disclosure.

10 Camera
20 Convolutional neural network model
21 Processing unit
22 Convolutional layer
23 Activation layer
24 Pooling layer
25 Fully connected layer
30 Speaker
40 Microphone
50 Voice dialogue module
52 Voice synthesis unit
54 Voice recognition unit
56 Natural language processing unit
60 Processor unit
62 Operation display screen
P1 Facial image information
P2 Facial feature information.

DETAILED DESCRIPTION OF THE DISCLOSURE

To understand the technical features, objectives, and effects of the present disclosure more clearly, a description on specific implementations of the present disclosure is made now with reference to accompanying drawings. The same reference numbers in each drawing refer to components with same structures or components with similar structures and same functions.

In this specification, "schematic" indicates "serving as an example, a case, or description", and any illustration or implementation described as "schematic" in this specification should not be interpreted as a more preferred or more advantageous technical solution.

For brevity of the accompanying drawings, parts related to the present disclosure are schematically shown in the accompanying drawings, and do not represent an actual structure as a product.

FIG. 1 illustrates a flowchart of a schematic implementation of a method for assisting in determining an identity of a scanned person in CT scanning. Referring to FIG. 1, the method for assisting in determining an identity of a scanned person in CT scanning includes the following steps:

S10: Obtain identity information of a scanned person. The identity information of the scanned person generally may be inputted in a management system of a hospital before the scanned person enters CT scanning room, and can be extracted from the management system of the hospital directly. The identity information of the scanned person includes, but is not limited to, name, gender, and age.

Figure 2:
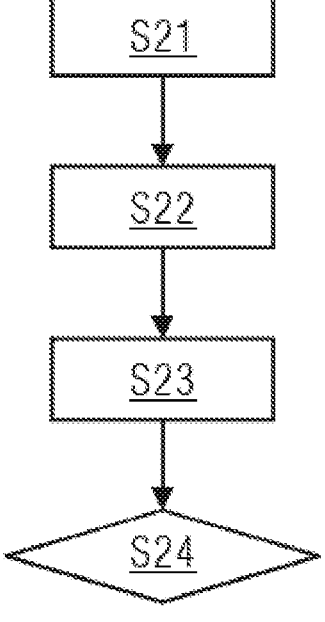
FIG. 2 illustrates a flowchart of a schematic implementation of using a facial recognition algorithm, in accordance with one or more embodiments of the present disclosure.

S20: Collect facial image information P1 of the scanned person after the scanned person is positioned, and determine whether the scanned person is a match based on the identity information of the scanned person by using a facial recognition algorithm. FIG. 2 is a flowchart of a schematic implementation of using a facial recognition algorithm. Referring to FIG. 2, step S20 specifically includes the following steps:

S21: Photograph the scanned person through a camera 10 to collect the facial image information. An existing CT scanner may be configured with a camera for observing a scanned person during a scan. The facial image information P1 may be captured by using the camera of the CT scanner through AI technology. Certainly, the camera may be arranged separately, and the camera can be disposed to face the face of the scanned person and to directly collect the facial image information after the scanned person is so positioned.

S22: Build a convolutional neural network model 20 based on a vision hardware platform and input the identity information of the scanned person and the facial image information P1. The vision hardware platform may be a computer, a cloud server, or a device with a SOC system. The convolutional neural network model 20 is a trained software program running on the vision hardware platform.

Figure 3:
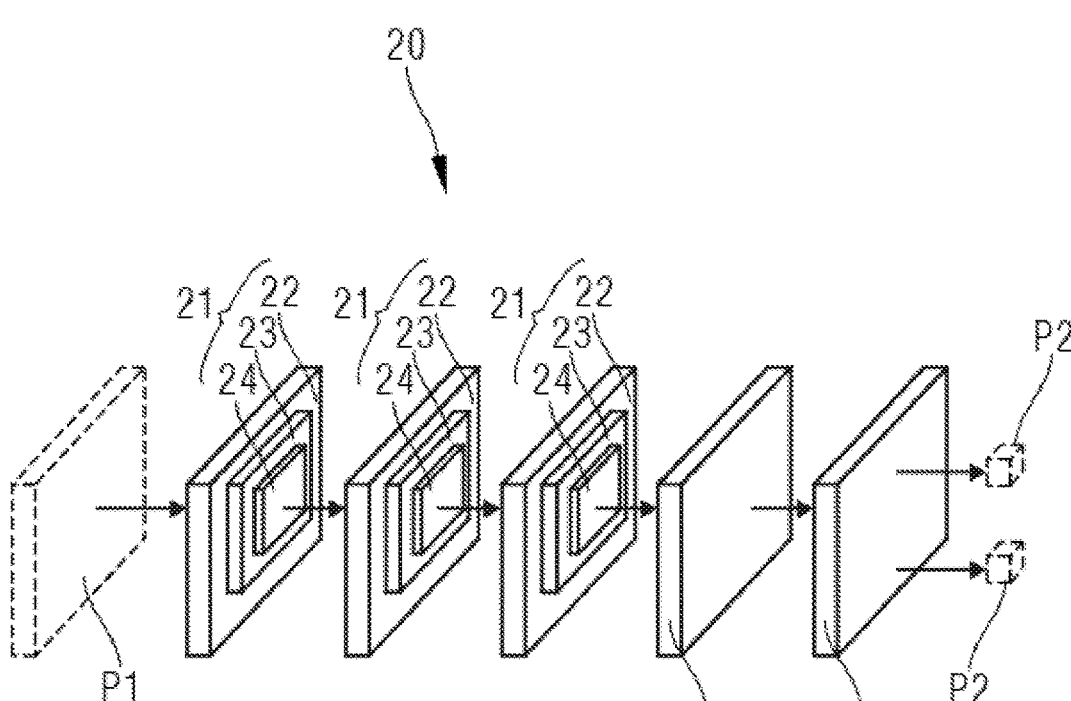
FIG. 3 illustrates a structural diagram of a schematic implementation of a convolutional neural network model, in accordance with one or more embodiments of the present disclosure.

S23: The vision hardware platform extracts facial feature information P2 corresponding to the identity information of the scanned person by using the convolutional neural network model 20. FIG. 3 is a structural diagram of a schematic implementation of a convolutional neural network model. Referring to FIG. 3, the convolutional neural network model 20 includes three processing units 21 and two fully connected layers 25 that are connected in series. Each of the processing units 21 includes a convolutional layer 22, an activation layer 23, and a pooling layer 24. A first convolutional layer 22 is used for inputting the facial image information P1 and extracting some low-level features, such as an edge, a line, and a corner. Three convolutional layers 22 iteratively extract more complex features from the low-level features. The activation layer 23 performs nonlinear mapping on the result of the convolutional layer 22 to avoid a lack of expressive power of a linear model. The pooling layer 24 compresses an input feature map to make the feature map smaller and to simplify the complexity of network computing. The fully connected layers 25 connect and classify all features. The last one of the fully connected layers 25 can output the facial feature information P2, and the facial feature information P2 includes, but is not limited to, gender and age.

S24: Compare the facial feature information P2 with the identity information of the scanned person, and determine whether the scanned person is a match according to a comparison result.

Figure 4:
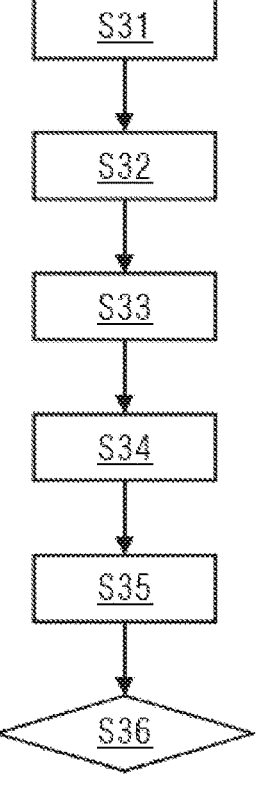
FIG. 4 illustrates a flowchart of a schematic implementation of using natural language processing technology, in accordance with one or more embodiments of the present disclosure.

S30: Perform a voice dialogue with the scanned person based on the identity information of the scanned person by using natural language processing technology after the scanned person is positioned, and determine whether the scanned person is a match. FIG. 4 is a flowchart of a schematic implementation of using natural language processing technology. Referring to FIG. 4, step S30 specifically includes the following steps:

S31: Build a voice dialogue module 50 based on a voice hardware platform and input the identity information of the scanned person. The voice hardware platform may be a computer, a cloud server, or a device with a SOC system. The voice dialogue module 50 is a software program running on the voice hardware platform.

Figure 5:
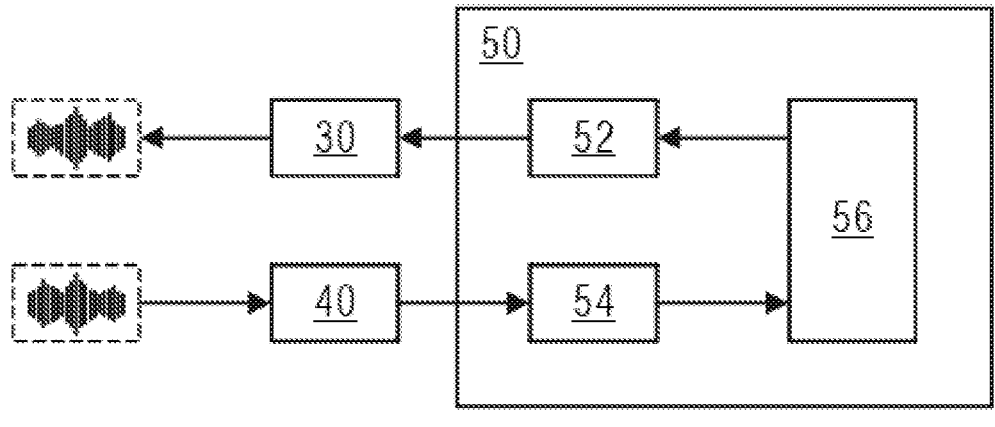
FIG. 5 illustrates a structural diagram of a schematic implementation of a voice dialogue module, in accordance with one or more embodiments of the present disclosure.

FIG. 5 illustrates a structural diagram of a schematic implementation of a voice dialogue module. Referring to FIG. 5, the voice dialogue module 50 includes a voice synthesis unit 52, a voice recognition unit 54, and a natural language processing unit 56. The voice synthesis unit 52 is configured to convert question information from a text information format into an audio information format. The voice recognition unit 54 is configured to receive an answer voice in an audio information format, and to convert the answer voice into answer information in a text information format. The natural language processing unit 56 is developed based on natural language processing (NLP) technology, and is configured to analyze the identity information of the scanned person and to transmit the question information to the voice synthesis unit 52. The natural language processing unit 56 is further configured to receive the answer information from the voice recognition unit 54, extract the voice feature information, compare the voice feature information with the identity information of the scanned person after analysis, and determine whether the scanned person is a match according to a comparison result.

S32: The voice dialogue module 50 analyzes the identity information of the scanned person and generates corresponding question information. Specifically, the identity information of the scanned person is analyzed by the natural language processing unit 56 and the question information is transmitted to the voice synthesis unit 52. The question information includes, but is not limited to, a question about the name, gender, and age of the scanned person.

S33: The voice dialogue module 50 plays the question information to the scanned person through a speaker 30. Specifically, the voice synthesis unit 52 converts the question information in the text information format into the question information in the audio information format and transmits the question information in the audio information format to the speaker 30 to generate sounds.

S34: The voice dialogue module 50 collects an answer voice of the scanned person through a microphone 40 and converts the answer voice into answer information. After hearing a question, the scanned person answers the question, and the voice is collected by the microphone 40. The voice recognition unit 54 receives the answer voice in the audio information format from the microphone 40 and converts the answer voice in the audio information format into the answer information in the text information format.

S35: The voice dialogue module 50 extracts voice feature information corresponding to the identity information of the scanned person in the answer information according to preset logic. Since the scanned person gives an answer through a natural language which is not standardized, after receiving the answer information from the voice recognition unit 54, the natural language processing unit 56 needs to analyze the answer information with reference to a local or cloud logic reasoning library to extract the voice feature information that accurately expresses the name, gender, and age.

S36: The voice dialogue module 50 compares the voice feature information with the identity information of the scanned person, and determines whether the scanned person is a match according to a comparison result. Specifically, the voice feature information is compared with the identity information of the scanned person by the natural language processing unit 56, and whether the scanned person is a match is determined according to the comparison result.

S40: If either of determining results of the above determining is mismatching, a reminder is sent for determining the identity of the scanned person to an operator. If both determining results of the above determining match, then the scan is started.

In the method for assisting in determining an identity of a scanned person in CT scanning provided by the present disclosure, a facial image of the scanned person can be analyzed by using a facial recognition algorithm before a scanning program is started, and voice question and answer is performed with the scanned person by using natural language processing technology. It is determined, based on two independent manners, whether the identity of the scanned person is a match. If either of the determining results are not matched, a reminder of determining the identity of the scanned person is sent to an operator, which ensures the accuracy of the determining results. The method for assisting in determining an identity of a scanned person in CT scanning can reduce the work intensity of the operator, increase work efficiency, prevent the occurrence of a false scan, and avoid diagnosis delay.

Figure 6:
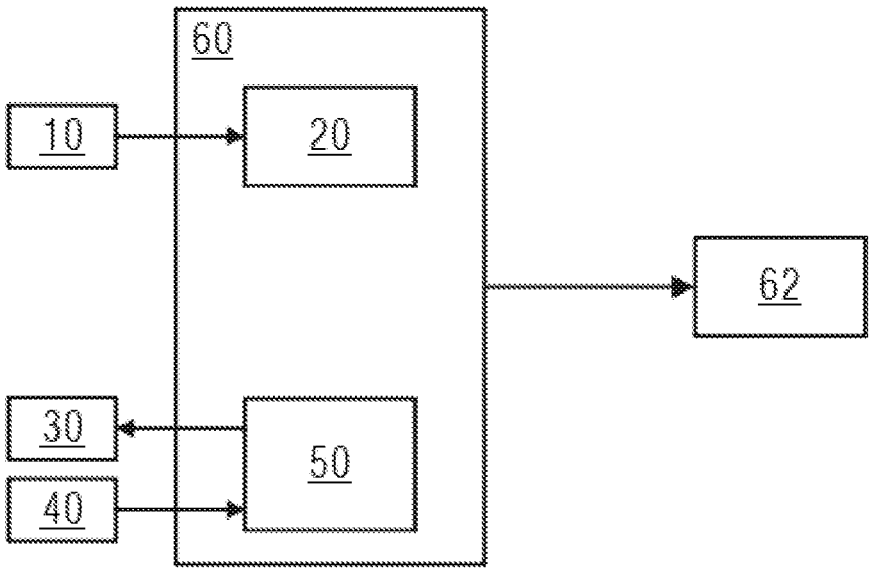
FIG. 6 illustrates a structural diagram of a schematic implementation of a system for assisting in determining an identity of a scanned person in CT scanning, in accordance with one or more embodiments of the present disclosure.

The present disclosure further provides a system for assisting in determining an identity of a scanned person in CT scanning. FIG. 6 illustrates a structural diagram of a schematic implementation of a system for assisting in determining an identity of a scanned person in CT scanning. Referring to FIG. 6, the system for assisting in determining an identity of a scanned person in CT scanning includes a camera 10, a vision hardware platform, a speaker 30, a microphone 40, a voice hardware platform, and a reminder device.

The camera 10 is configured to collect facial image information of a scanned person after the scanned person is positioned. The vision hardware platform may be a computer, a cloud server, or a device with a system on a chip (SoC) system. The vision hardware platform is implemented with a convolutional neural network model 20. The vision hardware platform is configured to receive the identity information of the scanned person and the facial image information P1, and extract facial feature information P2 corresponding to the identity information of the scanned person in the facial image information P1 through the convolutional neural network model 20; and the vision hardware platform is configured to compare the facial feature information P2 with the identity information of the scanned person, and generate an image mismatch signal in a case of mismatching.

In a schematic implementation, referring to FIG. 3 and FIG. 6, the convolutional neural network model 20 includes three processing units 21 and two fully connected layers 25 that are connected in series. Each of the processing units 21 includes a convolutional layer 22, an activation layer 23, and a pooling layer 24. A first convolutional layer 22 is used for inputting the facial image information P1 and extracting some low-level features, such as an edge, a line, and a corner. Three convolutional layers 22 iteratively extract more complicated features from the low-level features. The activation layer 23 performs nonlinear mapping on the result of the convolutional layer 22 to avoid a lack of expressive power of a linear model. The pooling layer 24 compresses an input feature map to make the feature map smaller and simplify the complexity of network computing. The fully connected layers 25 connect and classify all features. The last one of the fully connected layers 25 can input the facial feature information P2, and the facial feature information P2 includes, but not limited to, gender and age.

The speaker 30 is configured to receive a sound signal and play a voice. The microphone 40 is configured to receive a voice and convert the voice into a sound signal. The voice hardware platform may be a computer, a cloud server, or a device with a SOC system. The voice hardware platform is built with a voice dialogue module 50. The voice dialogue module is configured to receive the identity information of the scanned person, and convert question information corresponding to the identity information of the scanned person into a sound signal and transmit the sound signal to the speaker 30. The voice hardware platform is further configured to receive, through the microphone 40, a sound signal answered by the scanned person and extract voice feature information corresponding to the identity information of the scanned person. The voice hardware platform is configured to compare the voice feature information with the identity information of the scanned person, and generate a voice mismatch signal in a case of mismatching.

In a schematic implementation, referring to FIG. 5 and FIG. 6, the voice dialogue module 50 includes a voice synthesis unit 52, a voice recognition unit 54, and a natural language processing unit 56. The voice synthesis unit 52 is configured to convert question information from a text information format into an audio information format. The voice recognition unit 54 is configured to receive an answer voice in an audio information format, and convert the answer voice into answer information in a text information format. The natural language processing unit 56 is developed based on natural language processing (NLP) technology, and is configured to analyze the identity information of the scanned person and transmit the question information to the voice synthesis unit 52. The natural language processing unit 56 is further configured to receive the answer information from the voice recognition unit 54, extract the voice feature information and compare the voice feature information with the identity information of the scanned person after analysis, and determine whether the scanned person is a match according to a comparison result.

In a schematic implementation, the vision hardware platform and the voice hardware platform are a processor unit 60 of a CT scanner. The reminder device includes a processor unit 60 and an operation display screen 62 of a CT scanner. The processor unit 60 of the CT scanner can display a pop-up window to remind the operator through the operation display screen 62 when either of the image mismatch signal and the voice mismatch signal is generated. However, this is not limited herein. In other schematic implementations, the reminder device may also remind the operator in other manners, such as issuing a sound reminder through the speaker or issuing a light reminder through an LED light.

In the system for assisting in determining an identity of a scanned person in CT scanning provided by the present disclosure, a facial image of the scanned person can be analyzed by using a facial recognition algorithm before a scanning program is started, and voice question and answer is performed with the scanned person by using natural language processing technology. It is determined, based on two independent manners, whether the identity of the scanned person is a match. If either of the determining results is mismatching, a reminder of determining the identity of the scanned person is sent to an operator, which ensures the accuracy of the determining results. The above system for assisting in determining an identity of a scanned person in CT scanning can reduce the work intensity of the operator, increase work efficiency, prevent the occurrence of a false scan, and avoid diagnosis delay.

The present disclosure further provides a CT scanner, including the above system for assisting in determining an identity of a scanned person in CT scanning. The CT scanner can reduce the work intensity of the operator, increase work efficiency, prevent the occurrence of a false scan, and avoid diagnosis delay.

It should be understood that, although this specification is described according to each embodiment, each embodiment may not include only one independent technical solution. The description manner of this specification is merely for clarity. This specification should be considered as a whole by a person skilled in the art, and the technical solution in each embodiment may also be properly combined, to form other implementations that can be understood by the person skilled in the art.

A series of detailed descriptions listed above are only specific descriptions for feasible embodiments of the present disclosure, and are not used to limit the protection scope of the present disclosure. Equivalent embodiments or modifications made without departing from the technical spirit of the present disclosure, such as combination, division or repetition of features, all should be included within the protection scope of the present disclosure.

The various components described herein may be referred to as "units," "modules," or "systems." Such components may be implemented via any suitable combination of hardware and/or software components as applicable and/or known to achieve their intended respective functionality. This may include mechanical and/or electrical components, processors, processing circuitry, or other suitable hardware components, in addition to or instead of those discussed herein. Such components may be configured to operate independently, or configured to execute instructions or computer programs that are stored on a suitable computer-readable medium. Regardless of the particular implementation, such units, modules, and/or systems, as applicable and relevant, may alternatively be referred to herein as "circuitry," "controllers," "processors," or "processing circuitry," or alternatively as noted herein.

The invention claimed is:

1. A method for determining an identity of a person in computed tomography (CT) scanning, comprising:
obtaining identity information of a person;
collecting facial image information of the person after the person is positioned;
determining, using a facial recognition algorithm, whether the person is a match based on the identity information of the person;
performing, using natural language processing (NLP), a voice dialog with the person based on the identity information of the person after the person is positioned;
determining whether the person is a match based on the voice dialog;
in response to (i) the person being determined to not be a match based on the facial recognition algorithm, or (ii) the person being determined to not be a match based on the voice dialog, transmitting a reminder to an operator to determine an identity of the person; and
in response to (i) the person being determined to be a match based on the facial recognition algorithm, and (ii) the person being determined to be a match based on the voice dialog both, initiating a CT scan.

2. The method of claim 1, wherein the collecting the facial image information of the person and determining whether the person is a match based on the identity information of the person comprises:
photographing the person via a camera to collect the facial image information;
generating a convolutional neural network (CNN) model based on a vision hardware platform;

inputting the identity information of the person and the facial image information to the generated CNN model;

extracting, via the vision hardware platform, facial feature information corresponding to the identity information of the person using the CNN model;

comparing the facial feature information with the identity information of the person; and determining whether the person is a match according to a comparison result.

3. The method of claim 2, wherein the CNN model comprises three processing units and two fully connected layers that are connected in series, each of the processing units comprising a convolutional layer, an activation layer, and a pooling layer, and a last one of the fully connected layers being configured to output the facial feature information.

4. The method of claim 1, wherein the performing the voice dialog with the person and determining whether the person is a match comprises:

inputting the identity information of the person into a voice dialog processor that is based on a voice hardware platform;

analyzing, by the voice dialog processor, the identity information of the person and generating corresponding question information;

playing, by the voice dialog processor, the question information to the person via a speaker;

collecting, by the voice dialog processor, an answer voice of the person via a microphone and converting the answer voice into answer information;

extracting, via the voice dialogue processor from the answer information, voice feature information corresponding to the identity information of the person according to preset logic;

comparing, by the voice dialog processor, the voice feature information with the identity information of the person; and determining whether the person is a match according to a comparison result.

5. The method of claim 4, wherein the voice dialog processor comprises:

a voice synthesizer configured to convert the question information from a text information format to an audio information format;

a voice recognizer configured to receive the answer voice in an audio information format, and to convert the answer voice into a text information format; and a natural language processor configured to analyze the identity information of the person and to transmit the question information to the voice synthesizer, wherein the natural language processor is further configured to:

receive the answer information from the voice recognizer;

extract the voice feature information from the answer information;

compare the voice feature information with the identity information of the person after analysis; and determine whether the person is a match according to a comparison result.

6. The method of claim 1, wherein the identity information of the person comprises one or more of name, gender, and/or age.

7. A system for determining an identity of a person in computed tomography (CT) scanning, comprising:

a camera configured to collect facial image information of a person after the person is positioned;

a vision hardware platform implementing a convolutional neural network (CNN) model, wherein the vision hardware platform is configured to:

receive identity information of the person and the facial image information;

extract facial feature information corresponding to the identity information of the person in the facial image information via the CNN model;

compare the facial feature information with the identity information of the person; and generate an image mismatch signal when a mismatch between the facial feature information with the identity information of the person is determined;

a speaker configured to receive a sound signal and to play a voice;

a microphone configured to receive a voice and to convert the voice into a sound signal;

a voice hardware platform implementing a voice dialog processor, wherein the voice dialog processor is configured to:

receive the identity information of the person;

convert question information corresponding to the identity information of the person into a sound signal; and transmit the sound signal to the speaker;

receive, via the microphone, an answer sound signal answered by the person;

extract, from the answer sound signal, voice feature information corresponding to the identity information of the person;

compare the voice feature information with the identity information of the person; and generate a voice mismatch signal when a mismatch between the voice feature information and the identity information of the person is determined; and reminder circuitry configured to transmit a reminder to determine an identity of the person to an operator in response to receiving the image mismatch signal or the voice mismatch signal.

8. The system of claim 7, wherein the CNN model comprises three processing units and two fully connected layers that are connected in series, each of the processing units comprising a convolutional layer, an activation layer, and a pooling layer, and a last one of the fully connected layers being configured to output the facial feature information.

9. The system of claim 7, wherein the voice dialog processor comprises:

a voice synthesizer configured to convert the question information from a text information format into an audio information format;

a voice recognizer configured to receive the answer sound signal to an audio information format, and to convert the answer sound signal into a text information format as answer information; and a natural language processor configured to analyze the identity information of the person and to transmit the question information to the voice synthesizer, wherein the natural language processor is further configured to:

receive the answer information from the voice recognizer;

extract the voice feature information from the answer information;

compare the voice feature information with the identity information of the person after analysis; and determine whether the person is a match according to a comparison result.

10. The system of claim 7, wherein the vision hardware platform and the voice hardware platform comprise a computer, a cloud server, or a device with a system on a chip (SoC).

11. The system of claim 10, wherein the vision hardware platform and the voice hardware platform comprise one or more processors of a CT scanner.

12. The system of claim 7, wherein the reminder circuitry comprises one or more processors and a display screen of a CT scanner.

13. The system of claim 7, wherein the system is part of a CT scanner.

* * * * *